United States Patent [19]

Yamanobe et al.

[11] Patent Number: 4,562,150

[45] Date of Patent: Dec. 31, 1985

[54] METHOD FOR MANUFACTURE OF CELLULASE

[75] Inventors: Takashi Yamanobe; Yasushi Mitsuishi, both of Ibaraki; Yoshiyuki Takasaki, Matsudo, all of Japan

[73] Assignees: Agency of Industrial Science and Technolgy; Ministry of International Trade and Industry, both of Tokyo, Japan

[21] Appl. No.: 586,723

[22] Filed: Mar. 6, 1984

[30] Foreign Application Priority Data

Mar. 9, 1983 [JP] Japan ................................ 58-38432
Mar. 9, 1983 [JP] Japan ................................ 58-38433
Mar. 9, 1983 [JP] Japan ................................ 58-38434

[51] Int. Cl.$^4$ .................. C12P 19/14; C12N 9/42; C12R 1/75
[52] U.S. Cl. ................................ 435/99; 435/209; 435/926
[58] Field of Search .................... 435/209, 926, 99

[56] References Cited

U.S. PATENT DOCUMENTS 4,081,328  3/1978  Skinner et al. .................. 435/209
4,275,163  6/1981  Gallo ............................... 435/209

*Primary Examiner*—Lionel M. Shapiro
*Attorney, Agent, or Firm*—Oblon, Fisher, Spivak, McClelland & Maier

[57] ABSTRACT

Cellulase is produced by culturing a strain of genus Acremonium in a culture medium and isolating produced cellulase from the culture medium.

3 Claims, 8 Drawing Figures

METHOD FOR MANUFACTURE OF CELLULASE

BACKGROUND OF THE INVENTION

This invention relates to a method for the manufacture of a cellulase by a strain of genus Acremonium and also embraces a method for the treatment of cellulose with the cellulase so manufactured.

"Cellulase" is a generic term for a group of enzymes which hydrolyze cellulose into glucose or cellobiose and cellooligomers. In this group, there are various enzymes which are specifically called by various designations such as $C_1$-enzyme, $C_x$-enzyme, and $\beta$-glucosidase or exo-$\beta$-glucanase, endo-$\beta$-glucanase, and cellobiase, depending on the modes of action for its substrate. The true nature of these enzymes has not yet been elucidated partly because various microorganisms produce cellulase and, consequently, there occur a wide variety of enzymes exhibiting dissimilar modes of activity upon crystalline cellulose, carboxymethyl cellulose, cellodextrin, cello-oligosaccharides, cellobiose, etc. and partly because celluloses are complicated structurally. In any event, the cellulase is an enzyme complex consisting of a plurality of enzymes which exhibit a harmonized interaction so as to hydrolyze a given cellulose into components such as glucose.

In recent years, cellulase has come to attract mounting attention from the standpoint of efficient utilization of biomass resources and has consequently become a major subject of study. The cellulase produced by the strains of genus Trichoderma and genus Aspergillus which have won widespread recognition still suffer from various drawbacks such as exhibiting insufficient hydrolyzing power upon native cellulose, failing to provide complete hydrolysis of cellulose into glucose, and giving rise to large amounts of cellobiose and cellooligosaccharides. Further, since virtually all types of cellulase heretofore known have been deficient in thermal stability, they can barely withstand protracted saccharification at temperatures on the order of 45° to 50° C. Thus, the reacting mixture being saccharified with such cellulase are likely to be contaminated by infectants during the course of the reaction.

SUMMARY OF THE INVENTION

A major object of this invention is to provide a method for the manufacture of cellulase which excels in ability to hydrolyze cellulose and in thermal stability.

To accomplish this object, therefore, this invention is directed to producing the cellulase by culturing in a medium a strain of genus Acremonium having an ability to produce cellulase and subsequently collecting the produced cellulase from the resultant culture broth. The cellulase produced by the strain of genus Acremonium exhibits strong hydrolyzing power on cellulose, permits the saccharification of cellulose to be carried out at temperatures 5° to 10° C. higher than the temperatures at which the saccharification has heretofore been performed by the use of conventional cellulase, and protects the reacting mixture for saccharification against otherwise possible contamination by infectants.

The other objects and characteristics of the present invention will become apparent to those skilled in the art from the further disclosure of the invention made in the following detailed description with reference to the accompanying drawings.

DESCRIPTION OF PREFERRED EMBODIMENT

Figure 1:
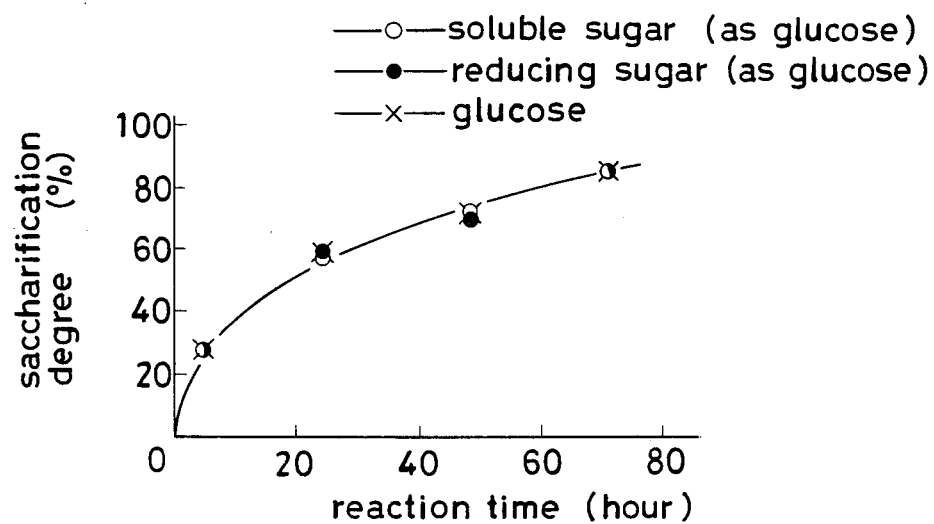
FIG. 1 is a graph showing the relation between the degree of saccharification and the reaction time during the course of saccharification of Avicel with the cellulase of this invention.

The inventors extensively searched the natural world for a microorganism capable of producing cellulase which exhibits outstanding hydrolyzing power on crystalline cellulose and a strong ability to saccharify the cellulose to glucose. They consequently isolated from soil a mold identified as a microorganism belonging to genus Acremonium and confirmed that the cellulase produced by this mold possesses strong hydrolyzing power on crystalline cellulose, exhibits notably higher $\beta$-glucosidase activity than the conventional well-known cellulase produced by the strain of *Trichoderma reesei*, for example, and therefore enjoys an unusually high saccharifying capacity which is sufficient for the cellulose to be hydrolyzed substantially completely to glucose. They have also demonstrated that since the cellulase produced by this mold excels in thermal stability, it permits the saccharification of the cellulose to be carried out at temperatures 5° to 10° C. higher than the highest temperatures at which the saccharification by the use of the conventional cellulase is carried out. The present invention has been perfected based on this knowledge.

The mycological properties of the cellulase-producing microorganism to be used in the present invention are as follows.

Growth: On malt extract agar, growth proceeds rapidly to reach a diameter of 70 mm in seven days at 30° C. Colonies are white at first and assume a slightly yellowish color afterward. Aerial hyphae slowly rise and assume a floccose appearance and occasionally form a ropy aggregate of hyphae. In the latter stage of culture, the rear sides of colonies assume a rosy brown to reddish brown color. Substantially similar growth proceeds on Czapek agar, though with smaller rise of aerial hyphae. The pH range for growth is 3.5 to 6.0, with the optimum pH falling near 4. The temperature range for growth is 15° C. to 43° C., with the optimum growth temperature falling near 30° C.

Morphology: Hyphae measure 0.5 to 2.5 $\mu$m in diameter, are colorless and contain septum. They have a smooth surface.

Conidia: Conidium-forming ability is extremely instable. Conidia readily disappear during sub-culture on Czapek agar and on malt extract agar medium. During isolation, conidiphores are observed to protrude from lateral sides of aerial hypha and are colorless. Conidia are in the shape of semi-spheres (2.5~5×2~4.5 μm) of smooth surface and are devoid of color. They are chained very loosely and are liable to disperse.

Referring to W. Gams, *Cephalosporium artige Schimmelpilge*, p. 84, G. Fisher (1971) and C. H. Dickinson, Mycol. Papers 115, p. 10 (1968) reveals that from the mycological properties described above it is proper for the microorganism in question to be identified as a mold closely related to genus Acremonium. Since no species of genus Acremonium has been known to possess a strong cellulase-producing property and further since the strain of the present invention produces a powerful and characteristic cellulase, this microorganism has been named *Acremonium cellulolyticus*.

This strain was deposited on Jan. 12, 1983 with the Fermentation Research Institute, Agency of Industrial Science & Technology, Tsukuba, Ibaraki-ken, Japan, under Deposit No. FERM P-6867 and also deposited under the Budapest Treaty on Mar. 1, 1984 and given Deposit No. FERM BP-495.

Genus Acremonium has been studied in detail by W. Gams. The genus formerly identified by the designation "Cephalosporium" has also been given careful review. As a result, the particular generic name "Acremonium" has been adopted recently. No other strain of genus Acremonium has been known to produce powerful cellulase, i.e. Avicelase or FP-ase, which can act upon crystalline cellulose.

For the production of cellulase by the aforementioned strain of genus Acremonium, this strain is required to be aerobically cultured at temperatures of about 20° to 40° C. for a period of about 2 to 15 days in a liquid or solid medium generally containing, as a carbon source, cellulose or a cellulose-containing substance such as Avicel, cotton, bagasse, or wheat bran and, as a nitrogen source, an organic or inorganic nitrogen-containing substance such as a nitrate, ammonium salt, urea, peptone, or yeast extract, and a small amount of a metal salt. Since the cellulase is an extracellular enzyme, it can be finally collected in the form of supernatant obtained by filtration of the culture broth in the case of liquid culture or in the form of enzyme solution obtained by extracting the culture solid with water or some other suitable inorganic salt solution in the case of solid culture.

The cellulase collected as described above manifests an outstanding saccharifying ability even on a highly crystallized cellulose such as Avicel. The product of this saccharification has a sugar composition which consists substantially wholly of glucose. This fact may well be cited as a major feature of the enzyme of the present invention. Table 1 compares the typical contents of FP-ase (filter paper degradation activity), CMC-ase, and β-glucosidase in the cellulase produced by the present invention with those in the cellulase produced by *Trichoderma reesei*.

TABLE 1

|  | Cellulase from *Trichoderma reesei* QM 9414 (Units/ml of medium) | Cellulase from the present invention (Units/ml of medium) |
|---|---|---|
| FP-ase | 5.1 | 5.7 |
| CMC-ase | 89 | 69.1 |
| β-Glucosidase | 0.3 | 30.9 |

Remarks:

(1) The data given in the table above concerning the cellulase from *Trichoderma reesei* QM 9414 have been cited from the information given in M. Mandels et al., Biotech. Bionez., XXIII 2009 (1981).

(2) The numerical value given under the heading "FP-ase" represents the enzymatic activity exhibited in hydrolyzing filter paper (1×6 cm) into reducing sugar. This enzymatic activity has been rated in accordance with J. Ferm. Tech., Vol. 54, page 267 (1976) and indicated in International Units (amount of enzyme for generating reducing power equivalent to 1 μmole of glucose per minute). It is generally held that Avicelase and FP-ase manifest equal enzymatic activity.

In the cellulase produced by *Trichoderma reesei* illustrated in Table 1, the FP-ase:CMC-ase:β-glucosidase ratio is 1:17.5:0.06, wherein in the cellulase produced by the microorganism of this invention, the aforementioned ratio is 1:12.1:5.4. As described, the composition ratio of FP-ase (or Avicelase):CMC-ase:β-glucosidase in the cellulase of the present invention generally falls in the range of 1:10–50:3–10, indicating that this enzyme has a notably high β-glucosidase content.

It is noted from this Table that the β-glucosidase activity manifested by the cellulase obtained by the present invention is notably high as compared with that manifested by the cellulase obtained by *Trichoderma reesei*. This fact is believed to explain why the product of saccharification of cellulose by the cellulase of this invention consists substantially wholly of glucose. Further, the β-glucosidase produced by this invention is a novel β-glucosidase which has notably greater substrate specificity than any of the types of β-glucosidase heretofore known to the art and which acts on cellobiose, also on cellooligosaccharides such as cellotriose, cellotetraose, and cellopentaose, on cellodextrin, and even on high-molecular cellulose such as Avicel and hydrolyzes them into glucose. Further, this cellulase is inhibited only to an insignificant degree by the glucose produced by the saccharification. This fact is also considered to contribute greatly to the outstanding saccharifying ability mentioned above.

FIG. 1 shows the amounts of reducing sugar, soluble sugar and glucose in the product of saccharification of Avicel with cellulase produced by the strain of genus Acremonium.

Avicelase was reacted with a suspension of 5% Avicel (0.05M acetate buffer, pH 4.5) in an amount corresponding to 40 units per g of Avicel. A given amount of the reaction solution was collected in 4, 24, 48 and 72 hours respectively. The amount of the reducing sugar was measured by the Somogyi-Nelson method with glucose as a standard, the amount of the soluble sugar by the phenol-sulfuric acid method with glucose as a standard, and the amount of the glucose by the glucose oxidase method respectively. The results revealed, as shown in FIG. 1, that the amounts were virtually the same, indicating that the soluble sugar in the saccharification product was almost glucose from the beginning of the reaction and that no accumulation of cellobiose and other oligosaccharides was recognized.

The sugar composition of the hydrolysate of cellulose produced by the cellulase of this invention is such that glucose accounts for 98 to 100% of the formed reducing sugar, whereas that of the saccharification product obtained by the cellulase of *Trichoderma reesei* is such that the ratio of cellobiose to glucose is reported to be in the range of 1:1 to 1:3 (J. Ferment. Technol., Vol. 54, page 267 (1976), etc.). For further hydrolysis of cellobiose to glucose, the β-glucosidase of *Aspergillus niger* which manifests outstanding hydrolyzing power on cellobiose is additionally used. The combined use of these two enzymes has found widespread acceptance (as reported in Applied Microbiology, Vol. 16, page 419 (1968), for example). The cellulase of the present invention amply contains β-glucosidase and, therefore, permits cellulose to be completely hydrolyzed into glucose without necessitating supply of β-glucosidase from any external source.

The cellulase produced as described above by the strain of genus Acremonium is an enzyme complex, namely, a group of three major enzyme components; $C_1$-enzyme represented by the enzyme acting on Avicel (a highly crystalline cellulose), namely Avicelase or FP-ase, $C_x$-enzyme represented by the so-called CMC-ase acting upon carboxymethyl cellulose (CMC), and β-glucosidase acting on cello-oligosaccharides such as cellobiose. Owing to the synergistic interaction of the group of these enzyme components, the cellulase of this invention provides complete hydrolysis of native cellulose into glucose. Now, the properties of these enzyme components will be described below.

(A) Enzymatic properties of Avicelase (1) Activity

Enzymes which act directly on insoluble crystalline cellulose such as cellulose powder, Avicel, absorbent cotton and filter paper and produce reducing sugars such as glucose and cellobiose have heretofore been called $C_1$ enzymes, FP-ase or Avicelase. These enzymes in common act directly insoluble cellulose and has an ability to hydrolyze the same. Therefore, these enzymes are called Avicelase throughout the specification.

(2) Working pH and optimum pH

Figure 2:
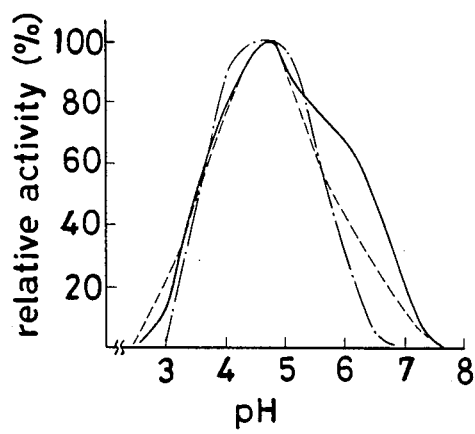
FIG. 2(a) is a graph showing the relation between the working pH and the activity of the cellulase according to the present invention.
FIG. 2(b) is a graph showing the relation between the working temperature and the activity of the cellulase of this invention.
FIG. 2(c) is a graph showing the pH stability of the cellulase of this invention.
FIG. 2(d) is a graph showing the thermal stability of the cellulase of the present invention.
Figure 2:
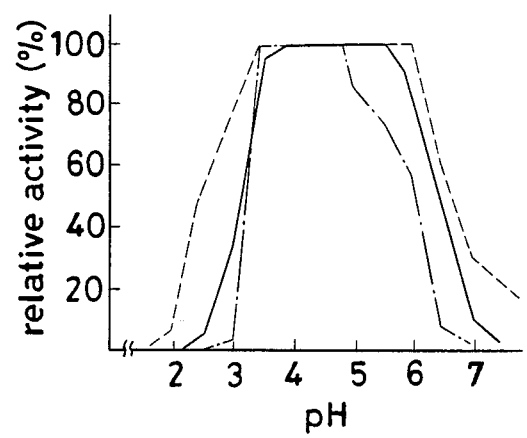
Figure 2:
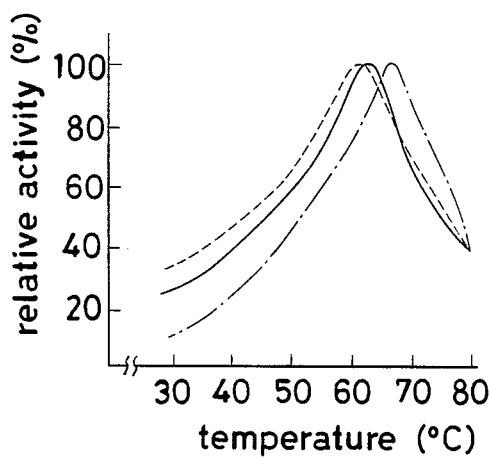
Figure 2:
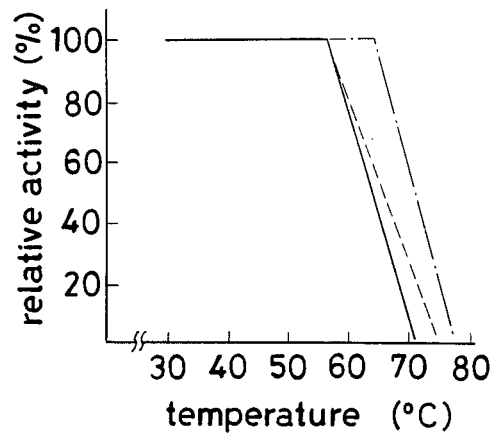

The working pH of this enzyme is found to fall in the range of 2 to 8 and the optimum pH thereof to fall near 4.5 as indicated by the solid line in FIG. 2(a).

(3) pH stability

The pH at which the enzyme, when left standing in the citrate-phosphate buffer at 45° C. for 20 hours, manifests stability is found to fall in the range of about 3.5 to about 5.5 as indicated by the solid line in FIG. 2(c).

(4) Range of working temperature and optimum temperature

The enzyme shows its activity intact at elevated temperatures up to about 90° C. This enzyme, when allowed to react with 1% Avicel in the presence of 0.05M acetate buffer (pH 4.5) for 10 minutes, is found to have its optimum working temperature near 65° C. as indicated by the solid line in FIG. 2(b).

(5) Thermal stability

When the enzyme is heated in 0.05M acetate buffer (pH 4.5) for 10 minutes, it undergoes substantially no inactivation at temperatures up to about 60° C. as indicated by the solid line in FIG. 2(d). It is inactivated to about 50% and about 80% respectively after 10 minutes' heating at 65° C. and 70° C.

(6) Inhibitors

This enzyme is strongly inhibited by mercury ions and copper ions both of concentrations of at least 1 mM, among other various metallic ions. It is also inhibited to about 80% by p-chloromercuric benzoate, an SH inhibitor, at a concentration of 1 mM.

(7) Method of purification

This enzyme can be purified by desalting and concentrating the culture filtrate with hollow fibers (Amicon HI-P5), separating the concentrated filtrate by column chromatography (NaCl 0→1M gradient) using DEAE-Sepharose (CL-6B), and treating the separated filtrate again by the same column chromatography (NaCl 0→0.6M gradient) system.

(8) Molecular weight

The molecular weight of this enzyme, when determined by the gel filtration method using a Bio-gel (A 0.5 m) column, is about 60,000.

(9) Method for determination of activity

The activity of this enzyme is determined by combining 0.5 ml of a suspension (pH 4.5) containing Avicel in a concentration of 0.5% in 0.1M acetate buffer (pH 4.5) with a suitable amount of the enzyme solution, diluting the resultant mixture with distilled water to a total volume of 1.0 ml, heating the mixed solution at 50° C. to induce reaction of the enzyme upon Avicel, and measuring the amount of reducing sugar formed by the reaction according to the Somogyi-Nelson method.

The amount of the enzyme which generates reducing power equivalent to 1 μmole of glucose per minute is taken as 1 unit.

(B) Enzymatic properties of CMC-ase (1) Multiple forms of CMC-ase

By means of the disc gel electrophoresis, the CMC-ase is divided into at least four components, which are mutually discriminable by molecular weight and isoelectric point. The CMC-ase I has a molecular weight of about 60,000 and an isoelectric point of 5.08, II about 60,000 and 4.95, III about 55,000 and 4.60, and IV about 15,000 and 4.48 respectively. Thus, the CMC-ase is formed of a complex of such isozymes.

(2) Activity

CMC-ase I, II, III and IV act upon such soluble cellulose derivatives as CMC and hydrolyze them into glucose and cello-oligosaccharides.

(3) Working pH and optimum pH

The working pH of the CMC-ase complex is found to cover a wide range of 2 to 8 as indicated by the dotted line in FIG. 2(a) and the optimum pH thereof is found to be about 4.5.

(4) pH stability

The pH at which the CMC-ase complex, when left standing in the citrate-phosphate buffer at 45° C. for 20 hours, manifests stability is found to fall in the range of about 3.5 to about 6 as indicated by the dotted line in FIG. 2(c).

(5) Range of working temperature and optimum temperature

This CMC-ase complex shows its activity intact at elevated temperatures up to about 90° C. This complex, when allowed to react with 1% CMC in the presence of 0.05M acetate buffer (pH 4.5) for 10 minutes, is recognized to have its optimum working temperature near 60° C. as indicated by the dotted line in FIG. 2(b).

(6) Thermal stability

When this enzyme is heated in 0.05M acetate buffer (pH 4.5) for 10 minutes, it undergoes substantially no inactivation at temperatures up to about 60° C. as indicated by the dotted line in FIG. 2(d). It is inactivated to about 40% and about 70% respectively after 10 minutes' heating at 65° C. and 70° C.

(7) Inhibitors

This enzyme is strongly inhibited by mercury ions and copper ions both of concentrations of at least 1 mM among other various metallic ions.

(8) Method of purification

This enzyme can be purified and isolated into the component isozymes by desalting and concentrating the culture filtrate with hollow fibers (Amicon HI-P5), then separating the concentrated filtrate by column chromatography (NaCl O→1.0M gradient) using DEAE-Sepharose (CL-6B), and treating the separated filtrate by the same column chromatography system.

(9) Method for determination of activity

The activity of this enzyme is determined by combining 0.5 ml of a solution (pH 4.5) containing 1% CMC in 0.1M acetate buffer with a suitable amount of enzyme solution, diluting the resultant mixture with distilled water to a total volume of 1.0 ml, heating the diluted solution at 50° C. to induce reaction of the enzyme upon the CMC, and measuring the amount of produced reducing sugar by the Somogyi-Nelson Method.

The amount of the enzyme which generates reducing power equivalent to 1 μmole of glucose per minute is taken as 1 unit.

(C) Enzymatic properties of β-glucosidase (1) Activity

The β-glucosidase acts on cello-oligosaccharides, cellotriose, cellotetraose, cellopentaose, and cellohexaose and hydrolyzes them into glucose. It also acts on β-glucosides such as salicin or high-molecular cellulose such as Avicel but shows virtually no activity on CMC and HEC (hydroxyethyl cellulose). The Km values of this enzyme relative to salicin, cellobiose, cellotriose, cellotetraose, cellopentaose, and cellohexaose are 3.40, 2.26, 1.19, 0.82, 0.52, and 0.51 mM.

(2) Working pH and optimum pH

The working pH of this enzyme is found to fall in the range of 3 to 7 as indicated by the chain line in FIG. 2(a) and the optimum pH thereof to fall near 4.5.

(3) pH stability

The pH at which the enzyme, when left standing in the citrate-phosphate buffer at 45° C. for 20 hours, manifests stability is found to fall in the range of about 3.5 to about 5 as indicated by the chain line in FIG. 2(c).

(4) Range of working temperature and optimum temperature

The enzyme shows its activity intact at elevated temperatures up to about 90° C. This enzyme, when allowed to react with 1% salicin in the presence of 0.05M acetate buffer (pH 4.5) for 10 minutes, is recognized to have its optimum working temperature near 70° C. as indicated by the chain line in FIG. 2(b).

(5) Thermal stability

When this enzyme is heated in 0.05M acetate buffer (pH 4.5) for 10 minutes, it undergoes substantially no inactivation at temperatures up to about 60° C. as indicated by the chain line in FIG. 2(d). It is inactivated to about 40% and to about 90% or more respectively after 10 minutes' heating at 70° C. and 80° C.

(6) Inhibitors

This enzyme is strongly inhibited by mercury ions and copper ions both of concentrations of at least 1 mM among other various metallic ions. Further glucono-δ-lactone acts as an antagonistic inhibitor on the substrate.

(7) Method of purification

This enzyme can be purified to the degree of electrophoretic homogeneity by desalting and concentrating the culture filtrate with hollow fibers (Amicon HI-P5), separating the concentrated filtrate by column chromatography (NaCl O→1M gradient) using DEAE-Sepharose (CL-6B), and subjecting the active fraction to chromato-focusing (pH 6→4) and to gel filtration with Bio-gel(A 0.5 m).

(8) Molecular weight

The molecular weight of this enzyme, when determined by the gel filtration method using a Bio-gel (A 0.5 m) column, is about 120,000.

(9) Method for determination of activity

The activity of this enzyme is determined by combining 0.5 ml of a solution (pH 4.5) containing salicin in a concentration of 1% in 0.1M acetate buffer with a suitable amount of the enzyme solution, diluting the resultant mixture with distilled water to a total volume of 1.0 ml, heating the reaction mixture at 50° C. to induce reaction of the enzyme upon salicin, and measuring the amount of the produced reducing sugar by the Somogyi-Nelson method.

The amount of the enzyme which generates reducing power equivalent to 1 μmole of glucose per minute is taken as 1 unit.

The β-glucosidase of the present invention shows more affinity for oligosaccharides as cellohexaose and cellopentaose than for substrates of small molecular weights such as salicin and cellobiose. Further, this enzyme acts on substrates of large molecular weights such as Avicel. Particularly, the present invention is the first that has brought to light the presence of an enzyme possessing the substrate specificity of hydrolyzing cellobiose and also hydrolyzing Avicel to a considerable extent. Moreover, the product of the hydrolysis consists substantially wholly of glucose. Thus, the β-glucosidase produced by the microorganism of the present invention is a novel species of β-glucosidase heretofore unknown to the art and manifests a specific activity resembling the activity of glucoamylase upon starch. The inventors, therefore, have given to this enzyme the name "glucocellulase".

As described above, the cellulase produced by the microorganism of genus Acremonium as contemplated by the present invention is a novel cellulase complex containing a novel β-glucosidase.

Generally the saccharification of cellulose by the cellulase obtained as described is carried out at a pH in the range of 3 to 6, preferably 4 to 5, at temperatures in the range of 30° to 60° C.

Cellulose as the substrate for treatment includes not only pure cellulose obtained from woods, grass, cotton, etc. but also various kinds of cellulosic materials. Examples of the cellulosic materials usable as the substrate include agricultural residues such as rice straw, wheat straw, rice husk and bagasse, forage such as napier grass and cogon grass, sawdust, waste paper, and fiber materials. Since these cellulosic materials contain hemicellulose and lignin besides cellulose, these are required to undergo chemical pretreatment with an acid or alkali and/or physical pretreatment such as milling, irradiation, explosion, etc. depending on the kind of the cellulosic materials to thereby isolate some amount of hemicellulose and lignin therefrom for the purpose of enabling saccharification of the cellulosic materials to be carried out more efficiently.

Cellulase of the present invention can be used not only for the manufacture of glucose from cellulose or cellulosic materials, but also for the effective skinning of and for the effective extraction of useful components from grains such as rice, wheat, beans, etc., fruits, marine algae, or the like and can also be utilized in the pretreatment of forage for the purpose of enhancing the digestibility of the forage and directly as a digester.

In the aforementioned saccharifying reaction, the concentration of cellulose as a substrate is desired to be as high as possible and, in general, it falls in the range of from 5 to 30%.

Figure 3:
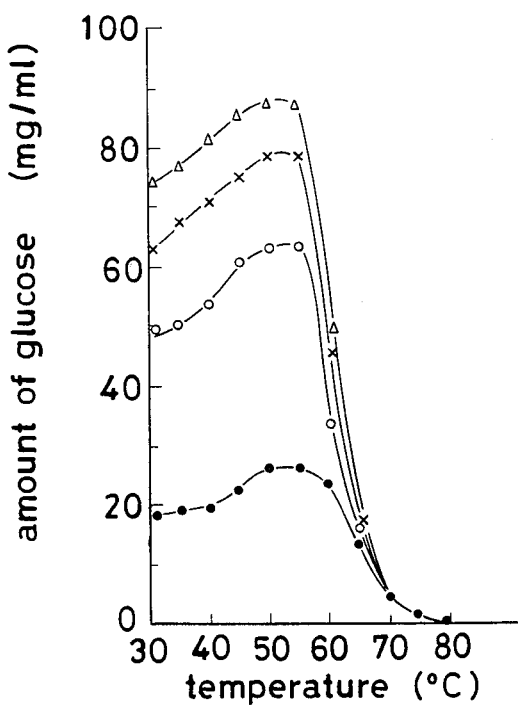
FIG. 3 is a graph showing the relation between the reaction temperature and the amount of glucose produced.

The relation between the reaction temperature and the amount of glucose produced when 10% Avicel was saccharified with cellulase of the present invention is graphically shown in FIG. 3, wherein the curve connecting solid circles (●) represents a 4-hour reaction, the curve connecting blank circles (o) represents a 24-hour reaction, the curve connecting cross marks (×) represents a 48-hour reaction, and the curve connecting triangle marks (Δ) represents a 72-hour reaction.

It will be noted from this graph that the cellulase of this invention can fulfill its function stably for a long period of reaction time at a temperature of 55° C. and enables the saccharifying reaction to proceed efficiently and that even at 60° C. the reaction can proceed over a comparatively long period of time. This indicates that the saccharifying reaction can be carried out at 5° to 10° C. higher temperatures than the 45° to 50° C. which is the upper limit of the reaction temperature in the saccharification by conventional cellulase of *Trichoderma reesei* (Biotechnol. Bioeng., Vol. 22, p. 326, 1980). Consequently, the otherwise possible contamination of the reacting mixture by infectants during the course of saccharification can be repressed and the reaction velocity can be heightened proportionately. In the hydrolysis of cellulose, therefore, the present invention brings about a notably high effect both technically and economically.

Now, the present invention will be described more specifically below with reference to examples. This invention is not limited to these examples.

EXAMPLE 1

In an Erlenmeyer flask having an inner volume of 200 ml, 20 ml of a culture medium (pH 4.0) containing 4% of cellulose, 1% of Bacto-peptone, 0.6% of potassium nitrate, 0.2% of urea, 0.16% of potassium chloride, 0.12% of magnesium sulfate, 1.2% of potassium 1 phosphate, $1 \times 10^{-3}\%$ of zinc sulfate, $1 \times 10^{-3}\%$ of manganese sulfate, and $1 \times 10^{-3}\%$ of copper sulfate was placed and sterilized by an ordinary method. In the sterilized culture medium, a strain of *Acremonium cellulolyticus* (FERM P-6867) inoculated thereto was aerobically cultured at 30° C. for six days. At the end of the culture, the culture broth was centrifuged to precipitate cells. The supernatant consequently obtained was tested for Avicelase activity, CMC-ase activity, and β-glucosidase activity. The results were 3.1 units/ml, 26.3 units/ml, and 138 units/ml respectively.

EXAMPLE 2

In a culture medium of the same composition as the culture medium of Example 1, except that 2% of bonito soluble was added in place of Bacto-peptone, a strain of *Acremonium cellulolyticus* (FERM P-6867) inoculated thereto was aerobically cultured at 30° C. for eight days. After the culture, the supernatant obtained by centrifuging the culture broth was tested for Avicelase, CMC-ase, and β-glucosidase activity. The results were 3.9 units/ml, 45.5 units/ml, and 21.1 units/ml respectively.

The supernatant of the culture broth was combined with cold acetone of a volume twice as large. The precipitate which consequently occurred in the resultant solution was collected by a centrifugal separator (9000 rpm for 10 minutes), dissolved in a small amount of water, and freed from insolubles, to afford clear concentrated enzyme solution. The ratios of recovery of Avicelase, CMC-ase, and β-glucosidase were 91.9%, 71.7%, and 96.8% respectively.

EXAMPLE 3

In a jar fermenter having an inner volume of 5 liters, 3 liters of a culture medium of the same composition as used in Example 1 was placed and sterilized at 121° C. for 30 minutes. In the sterilized culture medium, a strain of *Acremonium cellulolyticus* inoculated thereto was cultured as stirred at 700 rpm, with aeration continued at the rate of ½ vvm and pH controlled in the range of 3.8 to 5.0, for a period of six days.

The supernatant obtained by centrifuging the resultant culture broth was tested for Avicelase, CMC-ase, and β-glucosidase activity of the produced cellulase. The results were 14.1 units/ml, 162 units/ml, and 44 units/ml respectively.

EXAMPLE 4

A culture medium containing 4% of cellulose, 1.2% of $KH_2PO_4$, 1% of Bacto-peptone, $1 \times 10^{-3}\%$ of $ZnSO_4.7H_2O$, 0.6% of $KNO_3$, $1 \times 10^{-3}\%$ of $MnSO_4.7H_2O$, 0.2% of urea, $1 \times 10^{-3}\%$ of $CuSO_4.5H_2O$, 0.16% of KCl and 0.12% of $MgSO_4.7H_2O$ and adjusted to pH 4.0 was sterilized by an ordinary method. In the sterilized culture medium, a strain of *Acremonium cellulolyticus* (FERM P-6867) inoculated thereto was aerobically cultured at 30° C. for six days. After the culture, the supernatant obtained by centrifuging the culture broth was combined with cold acetone of a volume twice as large. The precipitate consequently formed in the resultant solution was collected by a centrifugal separator, dried, and put to storage.

An enzyme solution having 1 g of the dried enzyme dissolved in 150 ml of distilled water (containing 10.0 units of Avicelase per ml, 178 units of CMC-ase per ml, and 74.0 units of β-glucosidase per ml) was used in the saccharification described below.

One (1) g of cellulose powder was combined with different amounts of cellulase components indicated in Table 2. The resultant mixture was diluted to a total volume of 5 ml. The solution was adjusted to pH 4.5 and heated at 50° C. for 7, 24, and 48 hours to effect saccharification of the cellulose powder.

TABLE 2

| Cellulose powder | Avicelase | CMC-ase | β-Glucosidase |
|---|---|---|---|
| 1 (g) | 10 (units) | 178 (units) | 74 (units) |
| 1 | 20 | 357 | 147 |
| 1 | 40 | 714 | 294 |
| 1 | 80 | 1426 | 589 |

Figure 4:
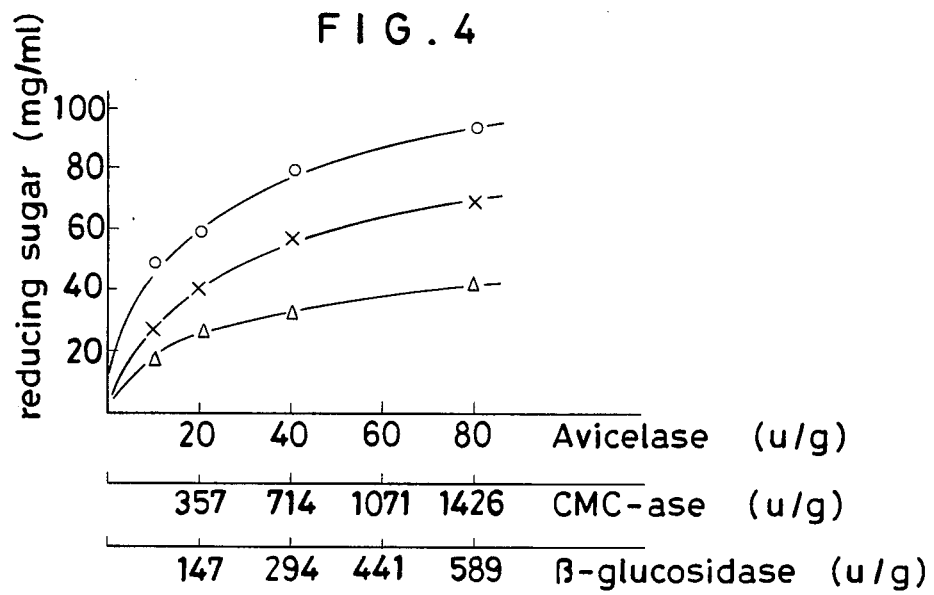
FIG. 4 is a graph showing the relation between the degree of cellulose saccharification and the amount of the cellulase added to the cellulose.

The saccharified solution was assayed for reducing sugar as glucose. The results were as shown in FIG. 4. In this graph, the curve connecting blank circles (o)

represents the results of 48 hours' saccharification, the curve connecting cross marks (×) represents the results of 24 hours' saccharification, and the curve connecting triangle marks (Δ) represents the results of 7 hours' saccharification. It is noted from this graph that when 80 units of Avicelase (in conjunction with 1426 units of CMC-ase and 589 units of β-glucosidase) were added per g of cellulose, the cellulose was substantially completely hydrolyzed in about two days. When the product of saccharification was assayed quantitatively for reducing sugar by the glucose oxidase method and the paper chromatographic method, the reducing sugar was found to consist substantially wholly of glucose.

EXAMPLE 5

One (1) g of cellulose powder was combined with the enzyme of Example 1 in an amount equivalent to 80 units of Avicelase (plus 1426 units of CMC-ase and 589 units of β-glucosidase). The resultant mixture was adjusted to pH 4.5 and heated at 50° C. to effect saccharification of the cellulose powder. At indicated intervals, the culture broth was sampled in a prescribed amount and assayed for reducing sugar (as glucose) and soluble sugar (as glucose) and glucose. The results were as shown in Table 3.

TABLE 3

| Time of saccharification (hours) | Glucose (mg/ml) | Reducing sugar (mg/ml) | Soluble sugar (mg/ml) |
|---|---|---|---|
| 7 | 51 | 50.2 | 50.3 |
| 24 | 68.2 | 70.0 | 71.2 |
| 48 | 92.5 | 93.0 | 94.0 |

As is noted from the table, the amount of reducing sugar, that of soluble sugar, and that of glucose in the product of saccharification were virtually the same, indicating that the product consisted substantially wholly of glucose. When the product was analyzed by paper chromatography, the results showed perfect agreement with those described above.

EXAMPLE 6

Pulverized bagasse (about 0.5 mm in particle diameter) was immersed in an aqueous 1% sodium hydroxide solution at 30° C. for 24 hours. It was separated from the aqueous solution with a glass filter, washed with distilled water, and dried at 105° C.

Figure 5:
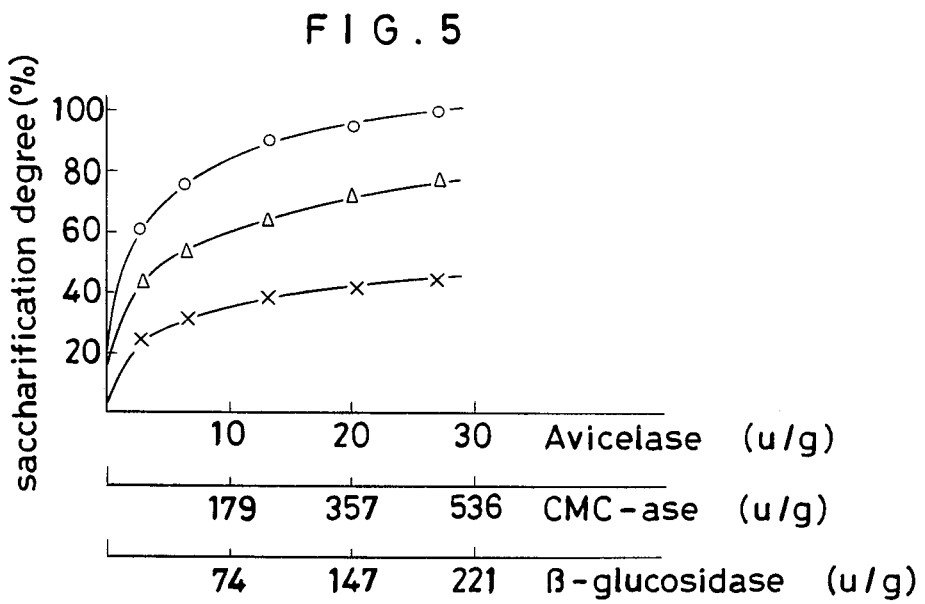
FIG. 5 is a graph showing the relation between the degree of saccharification of an alkali-treated bagasse and the amount of the cellulase added to the substrate.

A 1-g sample of the alkali-treated bagasse was combined with cellulase (in a different amounts equivalent to 3 to 28 units of Avicel per g of dried bagasse) prepared by use of *Acremonium cellulolyticus* (FERM P-6867). The resultant mixture was diluted to a total volume of 10 ml, adjusted to pH 4.5, and heated at 50° C. for 48 hours to effect saccharification of the bagasse. The resultant product of saccharification was assayed for reducing sugar, soluble sugar, and glucose. The results were as shown in FIG. 5. In the graph, the curve connecting blank circles (o) represents the results of soluble sugar as glucose, the curve connecting triangle marks (Δ) represents those of reducing sugar as glucose, and the curve connecting cross marks (×) represents those of glucose.

Here, the assay for reducing sugar was conducted by the Somogyi-Nelson method, that for total soluble sugar by the phenol-sulfuric acid method, and that for glucose by the glucose oxidase method respectively.

It has been confirmed that when 1 g of the alkali-treated bagasse is combined with 30 units of Avicelase and the resultant mixture is heated at 50° C. for about two days, the bagasse can be substantially perfectly saccharified.

What is claimed is:

1. A method for the manufacture of cellulase comprising the steps of culturing *Acremonium cellulolyticus* FERM P-6867 in a culture medium containing a carbon source, a nitrogen source, and a small amount of metal salt.

2. A method for the treatment of cellulose with cellulase, comprising the steps of culturing *Acremonium cellulolyticus* FERM P-6867 in a culture medium containing a carbon source, a nitrogen source, and a small amount of metal salt, thereby producing cellulase; collecting cellulase from said culture medium; and adding said cellulase to cellulose, thereby hydrolyzing cellulose into glucose.

3. The method of claim 2, wherein said hydrolysis of cellulose is carried out at a pH in the range of 4 to 6 and at a temperature in the range of 40° to 60° C.

* * * * *